United States Patent [19]

Weaver

[11] Patent Number: 4,643,968
[45] Date of Patent: Feb. 17, 1987

[54] PROCESS FOR DETERMINING METABOLISM AND GROWTH OF CELLS UNDER VARIOUS CONDITIONS

[75] Inventor: James C. Weaver, Sudbury, Mass.

[73] Assignee: Massachusetts Institute of Technology, Cambridge, Mass.

[21] Appl. No.: 527,436

[22] Filed: Aug. 26, 1983

Related U.S. Application Data

[63] Continuation-in-part of Ser. No. 229,483, Jan. 29, 1981, Pat. No. 4,401,755.

[51] Int. Cl.[4] ............... C12Q 1/18; C12Q 1/02; C12Q 1/06; C12N 11/02
[52] U.S. Cl. ............................. 435/32; 435/29; 435/39; 435/177
[58] Field of Search ............... 435/29, 32, 177, 34, 435/39

[56] References Cited

U.S. PATENT DOCUMENTS

| | | | |
|---|---|---|---|
| 4,061,466 | 12/1977 | Sjohölm et al. | 435/182 |
| 4,242,447 | 12/1980 | Findl et al. | 435/291 |
| 4,391,909 | 7/1983 | Lim | 435/182 |
| 4,401,755 | 8/1983 | Weaver | 435/34 |

FOREIGN PATENT DOCUMENTS

| | | | |
|---|---|---|---|
| 0075215 | 3/1983 | European Pat. Off. | 435/32 |
| 0099195 | 6/1982 | Japan | 435/182 |
| WO83/03102 | 9/1983 | PCT Int'l Appl. | 435/182 |

OTHER PUBLICATIONS

Some Methods for Microbiological Assay, Board, R. G., and Lovelock, D. W., eds., Academic Press (1975), p. 23.

Primary Examiner—Robert J. Warden
Assistant Examiner—Stephen C. Wieder
Attorney, Agent, or Firm—Paul J. Cook

[57] ABSTRACT

The metabolism and growth of cells is measured by suspending the cells in a liquid medium capable of forming a gel. The resultant suspension is formed into small droplets which droplets are caused to gel. Samples of the gel microdroplets (GMDs) are treated to alter the metabolism or growth of the cells, and the amount of metabolites, or other cellular products or external reaction products within each GMD is measured. The process can be utilized to determine essentially simultaneously the enumeration or count and the antibiotic susceptibility, or susceptibility to other compounds, factors, biological agents or other cells, of the cells which are representative of a larger sample of said cells.

10 Claims, No Drawings

PROCESS FOR DETERMINING METABOLISM AND GROWTH OF CELLS UNDER VARIOUS CONDITIONS

REFERENCE TO RELATED APPLICATION

This application is a continuation-in-part of application Ser. No. 229,483, filed Jan. 29, 1981 now U.S. Pat. No. 4,401,755.

BACKGROUND OF THE INVENTION

This invention relates to a process of performing measurements of cell metabolism and cell growth under different conditions.

Presently, in the field of rapid detection or measurement of microbial activity, and in the rapid detection or measurement of susceptibility of microorganisms to molecules, agents, or other cells, there is available a wide variety of apparatus and processes. Generally, these are based on the measurement of the physical characteristics of many viable cells (microorganisms), the growth of individual cells into many viable cells, or the growth and metabolism of many viable cells, or the composition of many cells. Examples of measurements of the physical characteristics of many cells include light attenuation (turbidity), light scattering and viscosity. Examples of the measurement of the growth of individual cells into many cells includes culturation on a petri dish or other gel surface or culturation within a gel contained in an optically transparent capillary. Examples of the measurement of the growth and metabolism of many viable cells includes measurement of pH changes of the medium containing the viable cells, measurement of non-radioactive accumulated volatile metabolites in the headspace over a sample, measurement of heat production, or measurement of electrical conductivity of the medium containing the viable cells. An example of staining includes the measurement of fluorescent labeled antibody, the antibody binding to species specific surface antigens on the cells. An example of the measurement of the composition of many cells is pyrolysis/mass spectrometry, which method is destructive in that it rapidly fragments cells under conditions of high temperature.

While the present procedures are highly satisfactory in many respects, two important problems exist. First, procedures which measure the growth of individual cells into many cells, such as culturation in a gel, have the highly desirable feature that they do provide an enumeration or count of the original number of cells present in a sample, but have the undesirable feature that they require a long incubation time, often 12 to 48 hours, to obtain a measurable colony from an original cell. This long incubation is also required for the measurement of the physical characteristics of many cells for the composition of many cells since it is generally not possible to obtain a sufficiently pure sample, free of debris and other cell types, without culturation. Further, measurement of the metabolism of many cells also requires a lengthy incubation time if the cell density in the sample is initially small. Second, procedures which measure the physical characteristics of many cells, the composition of many cells or the growth and metabolism of many cells do not provide an enumeration or count of the cells present, since there is often considerable variability between the individual cells. An important example is a variable and unknown lag time which often occurs when measurement of growth and metabolism of many cells is employed with a sample containing a small initial number of cells. In this case, a variable lag time can lead to the inability to correlate the subsequently measured growth and metabolism of many cells with enumeration or count of the initial cells. A particularly undesirable occurrence is the presence of initially stressed or injured cells which have a long, but a priori unknown, lag time, since the result of the measurement in this case is a false negative.

Measurement of individual microbiologically active entities such as individual enzyme molecules has been proposed by Rotman, Proceedings National Academy of Sciences, Vol. 47, Pages 1981–1991, (1961), who discloses the formation of water droplets in oil which droplets contain a small number of enzymes. However, this procedure is very tedious, difficult to replicate and the enzymes are susceptible to migration from the droplets to the oil-water interface.

It would be desirable to provide a means for measuring cell metabolism or growth to provide a base count and for exposing cells from the same specimen as those from which the base count is made to one or a variety of compositions which affect cell metabolism or growth which is capable of permitting determination of the extent of the effect from the composition within a short time, e.g. 1–10 hours. Such a process would be useful in determining the susceptibility of cells to various antibiotics by exposing a sample of the cells of various antibiotics. Such a process would be useful in determining the mode of treatment of a patient who is the source of the cells, e.g. by treatment with an antibiotic which exhibits a desired effect on cell metabolism or growth.

SUMMARY OF THE INVENTION

In accordance with this invention, a sample of cells is suspended at a slightly to highly dilute concentration in a medium which can be subsequently converted to a gel medium. The suspending medium is capable of substantially preventing degradation of the cells or of supporting metabolism or growth of the cells. The dilute suspension is formed into small droplets such as by being forced through a nozzle to form a liquid stream which then is sheared to form small liquid droplets, each of which has a high probability of containing a desired small number, preferably one or less, of cells. Thus, for example, each droplet can contain zero or one cell of interest with or without microbiologically active molecules which coact with the cells of interest by regulating the degree of dilution of the liquid composition processed and the average size of droplets produced. The droplets formed then are changed in temperature or are directed into a second liquid or vapor medium wherein the droplets rapidly gel. The change in temperature or second vapor or liquid medium is capable of converting the droplets to gel form while preventing degradation of the cell. In a related process, the liquid droplets are caused to gel before encountering the second vapor or liquid medium. In this case, the gel microdroplets (GMDs) can be directed onto a solid surface.

Alternatively, GMDs can be produced by dispersion of the aqueous sample within an immiscible liquid such as a liquid hydrocarbon. The dispersion method results in an emulsion, whose liquid micro-droplets can be caused to gel, thereby generating GMDs. For example, agarose GMDs can be readily produced by dispersing a liquid medium in mineral oil by stirring, and then reducing the temperature of the stirred suspension below the gelation temperature for a few minutes. Because of the hysteresis of the gelation process, the resulting suspension of GMDs can be warmed above the gelation temperature. Examples of the dispersion method for producing gel beads which are somewhat larger, 100 micron diameter up to 5 mm diameter are described by Nilsson et al. [the full correct citation for this 1983 reference]. (1983).

The GMDs are treated in a manner to effect a desirable alteration of the cells such as by incubation or by exposure to conventional marker molecules such as a fluorescent stain or by exposure to a mutagenic environment or the like. Either before or after such treatment, the GMDs can be coated with a layer of material such that the layer is impermeable to small molecular weight metabolites or products of specific enzymes or the like. An exemplary method for providing a suitable impermeable layer is suspension of the GMDs in a liquid hydrocarbon such as mineral oil.

The GMDs then are separated into a plurality of samples one or more of which comprises one or more control samples, untreated with a composition which changes cellular metabolism or growth while each of the other samples is exposed to one or more compositions which can change the metabolism or growth of the cells. When there are sensitive cells present in the GMDs which produce metabolites, hormones, or other cellular product, either intracellular or extracellular, such that said metabolites, hormones or other cellular product can be measured, the growth, metabolism or secretory production of said cells can be compared to growth, metabolism or secretory production of cells in GMDs which do not contain the composition. By comparing the metabolite, hormone or other cellular product measurement of one or more controls to each of the other samples, one can determine the presence or absence, or the amount, of a particular microorganism in the control GMDs. When the cells are obtained from a patient this process provides a means for analyzing for the presence of one or more microorganisms within a relatively short time, e.g. 1-10 hours since the cells are confined within a small GMD volume wherein the metabolite, hormone or other cellular product is relatively high and affords relatively easy measurement.

Alternatively, once the presence or absence, or the number or concentration of a particular type of cell has been established, the same measurement can often be used to determine and classify the relative effect of the various compositions on the particular microorganisms.

DESCRIPTION OF SPECIFIC EMBODIMENTS

In accordance with this invention, samples which may contain microbiologically active materials such as macromolecules, viroids, viruses, bacteria, yeasts, molds, parasites, plant cells, mammalian cells and the like are suspended in an aqueous medium capable of gelation upon subsequent treatment of the suspending medium.

Suitable suspending media include water soluble natural gel material and synthetic water soluble polymers. Representative suitable materials include agarose, kappa-carrageenan, iota-carrageenan, sodium alginate, furcellaran, zein, succinylated zein, succinylated cellulose or the like. Representative suitable synthetic water soluble polymers include those formed from vinyl pyrolidone, ethyl succinate cellulose 2-methyl-5-vinyl pyrridine-methyl acrylate-methacrylic acid copolymer, vinyl alcohol, vinyl pyrridine, vinyl pyrridine-styrene copolymer or the like. The microbiologically active material is suspended in the suspending medium at a dilution which is selected using knowledge of the volume of the GMD to be produced and an estimate of the density or concentration of the cells in the first liquid medium.

The GMDs are formed so that there is a high probability that each GMD contains a desired number, usually one or less, of microbiologically active material. This can be effected by regulating the dilution of the liquid composition from which GMDs are produced, a knowledge of the size of the cells and the size of the GMDs to be produced. The regulation of these factors can be determined by conventional Poisson statistical analysis so that the number of GMDs containing more than the desired number of cells is more than two standard deviations from the mean. It is often desirable, for example, to isolate zero to one cell per GMD.

Gel material, nutrients, indicators and the composition affecting metabolism or growth in the non-control samples, can be incorporated in the suspending medium, in which case very little dilution may be desired. Thus, for example, when it is desired to have a high probability of zero to one cell per GMD, it is only necessary to dilute the sample by more than a factor of about 1.01, usually up to about 10 or larger if desired if the unknown cell concentration is believed to be large. For example, if the average volume ($V_{gmd}$) is about $10^7$ ml, corresponding to a GMD with diameter about $5 \times 10^{-3}$ cm (50 microns), if spherical, dilution is generally not needed until the initial cell concentration reaches about $1 \times 10^{-7}$ cells/ml, which is a much higher concentration than encountered for most samples. For smaller spherical GMDs, for example, 10 micron diameter, dilution is not needed until the sample concentration reaches about $1 \times 10^{-9}$ cells/ml.

For purposes of measuring cell metabolism or growth, it is often desirable to utilize dilutions such that the suspension can be subsequently formed into droplets each of which has a high probability of containing none of the cells of interest or only a single cell of interest. By separating and localizing the cell in this manner, it is possible to measure materials of desired activity which activity is not diluted by the presence of other inert or biologically active material not having the desired activity. For example, it may be desirable to determine the effect of compositions on cells such as the bacterium *E. coli* in accordance with the process of this invention. A sample containing the bacteria is suspended in a medium capable of forming a gel upon subsequent treatment and then converted into liquid droplets such that there is a high probability that each droplet contains none or only one bacterial cell. According to one procedure for producing GMDs, the thus-produced liquid droplets are directed into a liquid medium capable of effecting gelation of the droplets, or the initially liquid droplets are changed in temperature or contacted with suitable gel-inducing vapors before entering a second liquid medium. Alternatively, the liquid sample containing the bacteria can be combined with a medium containing a temperature gelled material such as agarose, and the resulting liquid dispersed in a hydrocarbon liquid such as mineral oil. The resulting dispersion can then be cooled briefly, for a few minutes, such that GMDs are produced, and then warmed to a suitable temperature for incubation so as to encourage metabolism and growth of the bacterial cells. In addition, the GMDs also can contain a conventional or modified bacterial metabolism or bacterial growth supporting composition which permits the bacteria to metabolize and grow, and, sometimes if desired, to replicate within the GMDs, and can also contain indicator compounds such as dyes whose fluorescence or absorbence changes with pH or other properties of the environment within the GMDs.

In the case of uncoated GMDs, the suspension of such GMDs then is treated in a conventional manner such as with a fluorescent dye, a fluorescent labeled antibody or fluorescent labeled antigen or the like in order to mark the GMDs having bacteria whose measurement is desired while preventing or greatly reducing marking of the GMDs not containing the desired bacteria. In the case of coated GMDs, the first suspending medium is provided with specific nutrients or specific substrates or the effecting composition or the like, in addition to any indicator dyes for pH shifts, or other physical or chemical properties which affect an indicator dye, in order to allow measurement of metabolism or growth within a CMD.

This invention is useful for studying the effects of a wide variety of compositions on a wide variety of microbiologically active materials such as macromolecules, viroids, viruses, bacteria, yeasts, molds, parasites, plant cells, mammalian cells, and the like.

Representative bacteria for which the effect of introduced compositions can be measured include *E. coli, Bacillis Subtilis, Pseudomonas species, Clostridium thermocellum, Zymomanas mobilis, Methano bacterium sochngenic, Salmonella typhimurium, Serratic macens, Clostridium botulinum,* and *Bacillis sterothermophidis.* Conventional tagging means can be utilized in order to identify uncoated GMDs containing the bacteria having the desired characteristics including radioactively labeled antibody, fluorescent antibody labeling, use of fluorescent dyes, viable stains, and magnetic labeling of the GMDs. These procedures are well known to be selective in labeling and/or staining surface properties or internal pathways of bacteria. Similarly, the same or related techniques can be utilized for selectively determining the effects of compositions on macromolecules, viroids, viruses, parasites, yeats, molds, plant cells, mammalian cells, and the like.

After the biologically active material within the GMDs has been treated in order to effect the desired change in the material, such as by exposure to desired compositions followed by incubation with or without growth, mutation, staining with fluorescent stains, labeled with magnetically tagged or other immunological agents, the suspension of gel micro-droplets then is processed in an apparatus having the capability of sensing a physical characteristic of a sample of the GMDs to determine the presence or absence or quantity of a desired physical characteristic. The universe of GMDs then is divided into a plurality of subsamples, including one or more control samples each of which contains a plurality of GMDs. A base count or base enumeration is obtained, which comprises a measure of bacterial concentration. The remaining samples then are exposed to an antibiotic, usually with a series of different concentrations of each antibiotic in different samples, and, after a suitable time to permit the antibiotic to effect the bacteria, the metabolite or other cellular product concentration is measured for each sample. These latter measurements, when compared to the concentration of metabolite or cellular product in the control subsample from which the base count is determined gives an accurate measure of the degree of effectiveness of the particular antibiotic against the bacteria.

In another aspect, this process can be used to determine the antibiotic of choice to be given to a patient by processing a fluid or tissue sample from the patient in this manner, thereby determining the effective antibiotic(s) and then administering the antibiotic(s) to the patient. This procedure can be completed within a relatively short time, e.g. 1–10 hours.

The following example illustrates the present invention and is not intended to limit the same.

EXAMPLE I

In this examle, a sample containing a small but unknown number of a Bromothymol blue-tolerant strain of the bacterium *E. coli* was tested for the effect of three compositions: (1) sodium azide at a concentration of $10^{-2}$M, 2) the antibiotic chloramphenicol at a concentration of 0.1 microgram/ml, 3) chloramphenicol at a concentration of 100 microgram/ml, which bacterial species is known to generally be sensitive to the antibiotic chloramphenicol. The sample is diluted slightly, by a factor of about 1.01, by mixing the sample with a solution containing nutrient medium capable of supporting metabolism or growth of *E. coli*, a colorimetric pH indicator dye (brothymol blue), and agarose at 40 C. such that the final liquid mixture of sample plus eluant has nutrient concentrations of $NA_2HPO_4$ (sodium phosphate) at $4.2 \times 10^{-5}$M, $KH_2PO_4$ (potassium phosphate) at $2.2 \times 10^{-5}$M, $NH_4Cl$ (ammonium chloride) at $1.9 \times 10^{-2}$M, $MgSO_4$ (magnesium sulphate) at $1.0 \times 10^{-4}$M, $CaCl_2$ (calcium chloride) at $1.0 \times 10^{-6}$M, glucose at $5.0 \times 10^{-2}$M, supplemented with "Essential Amino Acid Mixture" (Whittaker M. A. Bioproducts) at a factor of 50 dilution, with "Essential Vitamin Mixture" (M. A. Bioproducts) at a factor 100 dilution, and the pH indicator dye Bromthymol blue at a concentration of $3.9 \times 10^{-3}$M, and agarose (Sigma, Type VII) at a concentration of about 1.5%. The sample is then subdivided into four subsamples, one of which is unaltered in order to serve as a control, while the compound sodium azide is added to the second subsample at a concentration of $10^{-2}$M, the antibiotic chloramphenicol to the third subsample at a concentration of 0.1 microgram/ml, and chloramphenicol to the fourth subsample at a concentration of 100 microgram/ml. Each subsample is then made into GMDs by dispersing the subsample in mineral oil, cooling the resulting suspension to about 4° C. for about 10 minutes, and then warming said suspension to 37° C. for incubation. After the first subsample has been so converted to GMDs, then the second subsample is similarly converted to GMDs using a second independent volume of mineral oil, and so on, until all four subsamples have been separately converted into independent subsamples of GMDs.

The GMDs of each independent subsample are maintained in suspension at 37° C., with small aliquots withdrawn periodically. The aliquots are placed on a glass microscope slide and individual GMDs exampled for changes in color or absorbency of the dye bromthymol blue. Unlike a fluorescent indicator, a colorimetric indicator is required to be present a relatively high concentration in order to provide observation of an absorbence based color change. The relatively high dye concentration contributes significantly to the buffering capacity of the environment within a GMD, and thereby gives rise to slower response times than can be obtained with a fluorescent indicator. Nevertheless, a color change from the initial blue at about pH 7.5 to a yellow corresponding to a pH of about 6.5 is observed in about 20% of the individual GMDs in the control (the first subsample) within eight hours. Since the average diameter of the GMDs is about 75 micron, the approximate 20% occupation of individual GMDs corresponds to a base count or base enumeration of about $1 \times 10^6$ cells/ml. For the second subsample in which cells are exposed to sodium azide at a concentration of $10^{-2}$M, no color change with time is observed over a 14 hour observation period, indicating (as expected) that sodium azide has a significant adverse effect on the cells' metabolism and growth. For the third subsample in which cells are exposed to chloramphenicol at a concentration of 0.1 microgram/ml somewhat less than 20% of the individuals GMDs are observed to have a color change from blue to yellow within a period of about ten hours, indicating that chloramphenicol at a concentration of 0.1 microgram/ml has a relatively negligible adverse effect on the cells metabolism and growth. For the fourth subsample in which cells are exposed to chloramphenicol at a concentration of 100 microgram/ml, essentially no GMDs are observed to exhibit a color change within a 14 hour observation time, indicating that chloramphenicol at a concentration of 100 microgram/ml has a significant adverse effect on the cells metabolism and growth.

I claim:

1. A process for determining the effects of at least one composition of matter upon a microbiologically active material selected from the group consisting of a macromolecule, a viroid, a virus, a bacterium, a yeast, a mold, a parasite, a plant cell and a mammalian cell in a sample comprising the steps of:

forming a plurality of subsamples from the sample of microbiologically active material comprising at least one test subsample and at least one control subsample, each of said subsamples being made by:

(i) forming a suspension of the microbiologically active material in a liquid diluent capable of forming a gel, each said suspension comprising a plurality of liquid micro-droplets, each of said liquid micro-droplets containing not substantially more than one microbiologically active entity;

(ii) converting said liquid micro-droplets of each said suspension into gel micro-droplets having a diameter between about 0.2 and 1000 microns;

combining said test subsamples with a composition of interest while maintaining said control subsamples as uncombined suspensions of micro-droplets;

measuring a characteristic product of microbiological activity for each of said combined subsamples and each of said uncombined subsamples; and comparing said measured characteristic product from said combined subsamples to said measured characteristic product from said uncombined subsamples to determine the effect of the composition of interest.

2. The process of claim 1 wherein said subsamples are formed prior to forming said gel micro-droplets.

3. The process of claim 1 wherein said subsamples are formed subsequent to forming said gel micro-droplets.

4. The process of claim 1 wherein said subsamples are combined with said composition of interest prior to forming said gel microdroplets.

5. The process of claim 1 wherein said subsamples are combined with said composition of interest subsequent to forming said gel micro-droplets.

6. The process of claim 1 wherein the microbiologically active material comprises at least one bacteria, and the composition of interest combined with said microbiologically active material comprises at least one antibiotic.

7. The process of claim 1 wherein said control subsamples comprise more than one medium for supporting metabolism and growth.

8. The process of claim 7 wherein the microbiologically active material is at least one type of bacteria.

9. The process of claim 7 wherein the microbiologically active material is at least one type of bacteria, and the composition of interest combined with said microbiologically active material is at least one antibiotic.

10. The process of any one of claims 1, 2, 3, 4, 5 and 7 wherein the composition of interest combined with said microbiologically active material comprises at least one cell which secretes a composition which biologically affects said microbiologically active material.

* * * * *